United States Patent
Uozumi et al.

(10) Patent No.: US 10,235,743 B2
(45) Date of Patent: Mar. 19, 2019

(54) MEASURING APPARATUS, MEASURING METHOD, AND PROGRAM

(71) Applicant: CANON KABUSHIKI KAISHA, Tokyo (JP)

(72) Inventors: Takayuki Uozumi, Utsunomiya (JP); Shigeki Kato, Shimotsuke (JP); Takashi Seki, Tokyo (JP); Yusuke Kasai, Saitama (JP)

(73) Assignee: Canon Kabushiki Kaisha, Tokyo (JP)

( * ) Notice: Subject to any disclaimer, the term of this patent is extended or adjusted under 35 U.S.C. 154(b) by 91 days.

(21) Appl. No.: 15/144,550

(22) Filed: May 2, 2016

(65) Prior Publication Data
US 2016/0335772 A1 Nov. 17, 2016

(30) Foreign Application Priority Data

May 11, 2015 (JP) .................................. 2015-096830

(51) Int. Cl.
*G01N 21/00* (2006.01)
*G06T 7/00* (2017.01)
(Continued)

(52) U.S. Cl.
CPC ............... *G06T 5/20* (2013.01); *G01N 21/55* (2013.01); *G01N 21/8422* (2013.01); *G06T 7/32* (2017.01);
(Continued)

(58) Field of Classification Search
None
See application file for complete search history.

(56) References Cited

U.S. PATENT DOCUMENTS 5,610,991 A * 3/1997 Janse .................. G10L 21/0208
381/13
5,694,484 A * 12/1997 Cottrell .................. G06T 5/002
382/167
(Continued)

FOREIGN PATENT DOCUMENTS

EP 2749865 * 7/2013
EP 2749865 A1 7/2014
(Continued)

OTHER PUBLICATIONS

Koichi Takase, et al., "Fast Estimation Algorithm for Calculation of Reflectance Map based on Wiener Estimation Technique", Optical Review, vol. 12, No. 1 (2005) pp. 20-24.
(Continued)

*Primary Examiner* — Shawn Decenzo
*Assistant Examiner* — Jarreas C Underwood
(74) *Attorney, Agent, or Firm* — Canon USA Inc., IP Division (57) ABSTRACT

A measuring apparatus includes an optical system configured to project light onto a sample and to receive light via the sample, an imaging device configured to take an image of a light source via the optical system, and a processor configured to obtain an optical characteristic of the sample based on an output of the imaging device. The processor is configured to determine a coefficient of a Wiener filter based on one of the image and a Fourier transform thereof and corresponding one of the light source (an aperture in an aperture unit) and a Fourier transform thereof, and obtain the optical characteristic based on the Wiener filter of which the coefficient has been determined, a Fourier transform of the image, and a Fourier transform of the light source.

11 Claims, 5 Drawing Sheets

(51) Int. Cl.
  *G06T 5/20* (2006.01)
  *G01N 21/84* (2006.01)
  *G01N 21/55* (2014.01)
  *G06T 7/32* (2017.01)
  *G06T 7/37* (2017.01)
  *G01N 21/57* (2006.01)

(52) U.S. Cl.
  CPC ............... *G06T 7/37* (2017.01); *G01N 21/57* (2013.01); *G01N 2021/8427* (2013.01)

(56) References Cited

U.S. PATENT DOCUMENTS

| | | | | |
|---|---|---|---|---|
| 6,201,601 | B1* | 3/2001 | Vaez-Iravani | G01J 3/44 356/237.4 |
| 6,542,248 | B1 | 4/2003 | Schwarz | |
| 6,608,676 | B1* | 8/2003 | Zhao | G01N 21/9501 250/559.27 |
| 6,757,065 | B1* | 6/2004 | Johansson | G01B 11/306 356/445 |
| 6,993,204 | B1* | 1/2006 | Yahil | G06T 5/20 382/205 |
| 7,181,085 | B1* | 2/2007 | Despain | H03H 21/0029 382/261 |
| 7,228,005 | B1* | 6/2007 | Yuan | G06K 9/40 382/280 |
| 7,636,489 | B2* | 12/2009 | Zimmer | G06T 5/20 382/254 |
| 7,767,950 | B2* | 8/2010 | Perlman | H04N 5/357 250/208.1 |
| 8,194,996 | B2* | 6/2012 | Hasegawa | G06K 9/40 348/208.4 |
| 8,294,958 | B2* | 10/2012 | Paterson | G01B 11/2518 358/1.9 |
| 9,235,283 | B2* | 1/2016 | Setlak | G06F 3/041 |
| 9,830,926 | B2* | 11/2017 | Helwani | G10L 21/0208 |
| 2005/0213841 | A1* | 9/2005 | Linguraru | G06K 9/40 382/261 |

FOREIGN PATENT DOCUMENTS

| | | |
|---|---|---|
| JP | 2008-256454 A | 10/2008 |
| JP | 2010-276492 A | 12/2010 |

OTHER PUBLICATIONS

Mark B. Cannell, et al., "Image Enhancement by Deconvolution", Handbook of Biological Confocal Microscopy, Third Edition, 488-500, 2006.

Philipp Urban, et al., "A Spatially Adaptive Wiener Filter for Reflectance Estimation", Researchgate, pp. 278-284, 16th Color Imaging Conference Final Program and Proceedings, pp. 279-284, 2008.

* cited by examiner

MEASURING APPARATUS, MEASURING METHOD, AND PROGRAM

BACKGROUND OF THE INVENTION

Field of the Invention

The present invention relates to, for example, a measuring apparatus for measuring an optical characteristic of a sample.

Description of the Related Art

Conventionally, for the purpose of evaluating the appearances of print materials, coated surfaces, and products, for example, standards for evaluating the optical characteristic of samples (their surfaces, their interiors, and so on) are being defined by JIS and ISO. For example, ISO 2813 and JIS Z 8741 define the specular gloss. ASTM E430 defines the haze and the distinctness of image (DOI). In addition, JIS K 7374 and ASTM D5767 define the image clarity. Furthermore, a unique index for evaluating the glossiness is also being proposed. Measuring apparatuses that obtain such a diffusion characteristic or an optical characteristic of samples are known. Such measuring apparatuses include an apparatus configured in accordance with a specific standard. Meanwhile, such measuring apparatuses include an apparatus that first obtains the diffusion characteristic (e.g., a bidirectional reflectance distribution function (abbreviated as BRDF)). This apparatus may function as a general-purpose apparatus that obtains a plurality of additional indices (e.g., the specular gloss, the haze, and the image clarity) on the basis of the diffusion characteristic. In an optical system in such a general-purpose measuring apparatus, a sample may be disposed in the pupil, a secondary light source may be provided at the anterior focal point, and an image sensor may be provided at the posterior focal point.

Japanese Patent Laid-Open No. 2010-276492 discloses an apparatus in which a pinhole serves as a secondary light source and an image of the pinhole is taken by an image sensor. Since the pinhole serves as the secondary light source, the diffusion characteristic with a high angular resolution can be obtained, but this apparatus may suffer from a disadvantage in securing the quantity of light or the luminous sensitivity. Meanwhile, Japanese Patent Laid-Open No. 2008-256454 discloses an apparatus in which an aperture in an aperture plate serves as a secondary light source and an image of the aperture is taken by an image sensor.

Increasing the angle of the aperture in the aperture plate provides an advantage in securing the quantity of light but suffers from a disadvantage in the angular resolution of the obtained optical characteristic, such as the diffusion characteristic.

SUMMARY OF THE INVENTION

The present invention provides, for example, a measuring apparatus advantageous in angular resolution of an obtained optical characteristic.

An aspect of the present invention provides a measuring apparatus that includes an optical system configured to project light onto a sample and to receive light via the sample, an imaging device configured to take an image of a light source via the optical system, and a processor configured to obtain an optical characteristic of the sample based on an output of the imaging device. The processor is configured to determine a coefficient of a Wiener filter based on one of the image and a Fourier transform thereof and corresponding one of the light source and a Fourier transform thereof, and obtain the optical characteristic based on the Wiener filter of which the coefficient has been determined, a Fourier transform of the image, and a Fourier transform of the light source.

Further features of the present invention will become apparent from the following description of exemplary embodiments with reference to the attached drawings.

DESCRIPTION OF THE EMBODIMENTS

Hereinafter, exemplary embodiments of the present invention will be described with reference to the accompanying drawings. It is to be noted that, throughout the drawings for describing the exemplary embodiments, in general (unless indicated otherwise), identical members are given identical reference characters, and duplicate descriptions thereof will be omitted.

First Exemplary Embodiment

Figure 1A:
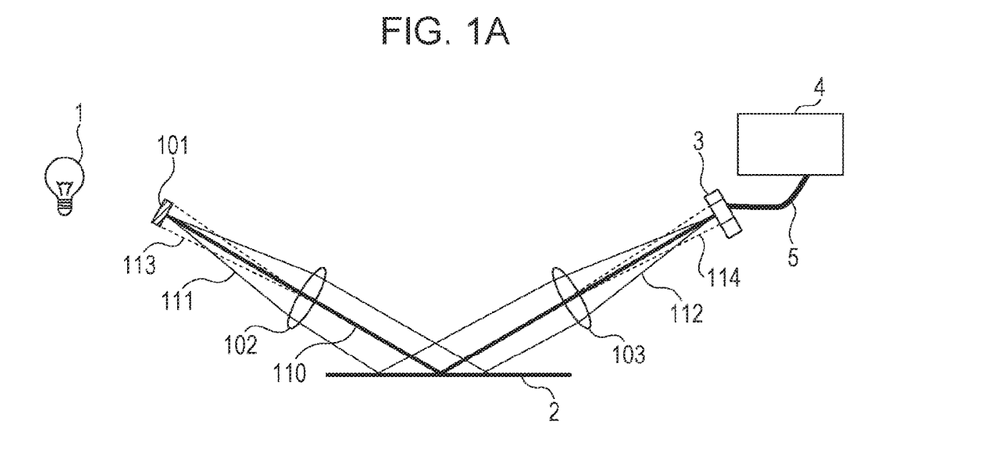
FIG. 1A illustrates a configuration example of a measuring apparatus.

FIG. 1A illustrates a configuration example of a measuring apparatus according to an exemplary embodiment. FIG. 1A is a sectional view of the measuring apparatus. The measuring apparatus includes an optical system (having an optical axis 110) that includes an aperture unit 101 having an aperture (also referred to as a light source or a secondary light source) and condenser lenses 102 and 103. The optical system projects light onto a sample 2 and receives light via the sample 2. A light source 1 (a real light source or a primary light source) illuminates the aperture in the aperture unit 101, for example, via another optical system (not illustrated). The sample 2 is disposed in the pupil (or at a position near the pupil) of the optical system. An imaging device 3 takes an image of the aperture (light source) in the aperture unit 101 via the optical system. The condenser lens 103 is configured to receive specular reflection light (112) produced as light (111) from the condenser lens 102 is specularly reflected by the sample 2. The aperture in the aperture unit 101 has an angle of aperture (angle of aperture on the light-projection side) 113 as viewed from the condenser lens 102. In addition, the light-receiving area of the imaging device 3 has an angle of aperture (angle of aperture on the light-receiving side) 114 as viewed from the condenser lens 103, and the stated angle of aperture 114 is determined by the product of the optical magnification of the optical system and the angle of aperture 113 on the light-projection side. It is preferable that the aperture unit 101 and the imaging device 3 be in an optically conjugate relationship. The imaging device 3 may include a solid-state image sensor of a charge-coupled device (CCD) or complementary metal-oxide semiconductor (CMOS) structure. In particular, a structure in which pixels are arranged in a matrix is preferable. The imaging device 3 is connected to a (signal) processor 4 (arithmetic device) via a cable 5. The processor 4 obtains the optical characteristic (e.g., diffusion characteristic) of the sample 2 on the basis of an output (signal) from the imaging device 3. The processor 4 may include, but is not limited to, a computer (or an information processing device that includes a device (processor or the like), such as a central processing unit (CPU)) that operates in accordance with a program corresponding to the flow of the process illustrated in FIG. 1B, FIG. 4, or FIG. 6, which will be described later.

Figure 1B:
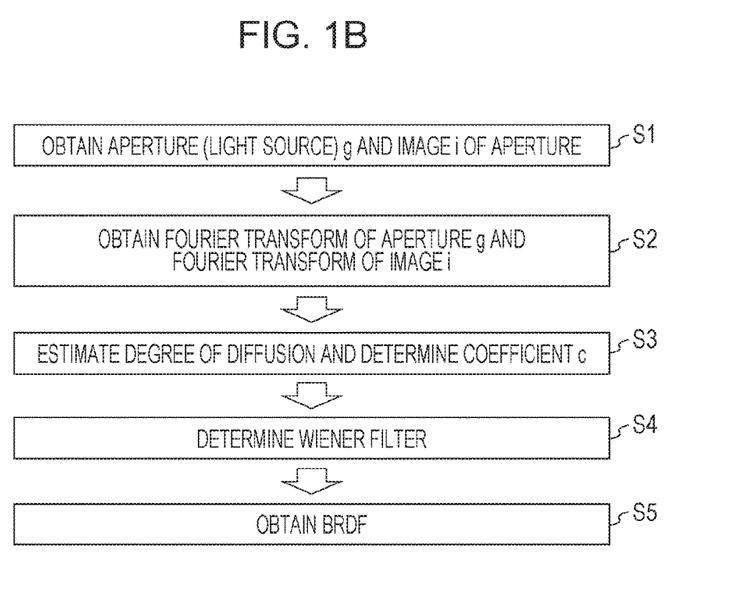
FIG. 1B illustrates a flow of a process executed by a processor.

FIG. 1B illustrates a flow of a process executed by the processor 4. Referring to FIG. 1B, in step S1, information on the aperture g(x,y) in the aperture unit 101 and information on an image i(x,y) of the aperture taken by the imaging device 3 via the sample 2 are obtained. For simplicity, g(x,y) and i(x,y) are also referred to as g and i, respectively. The information on the aperture g may be a signal to be obtained by the imaging device 3 when the sample 2 is replaced with a mirror surface, or may be a signal to be obtained by directly imaging the aperture with another imaging device.

In step S2, the aperture g and the image i are subjected to a Fourier transform so as to obtain G(m,n) and I(m,n). For simplicity, G(m,n) and I(m,n) are also referred to as G and I, respectively. A Fourier transform B(m,n) (also referred to simply as B for simplicity) of a BRDF serving as an optical characteristic can be expressed through the following relation with the use of G and I.

$$B(m, n) = \sum_{n=0}^{N_n-1} \sum_{m=0}^{N_m-1} \frac{I(m, n)}{G(m, n)} \exp\left[\frac{-i2\pi N_{m0}}{N_m} + \frac{-i2\pi N_{n0}}{N_n}\right] \quad (1)$$

In the above, $N_m$ and $N_n$ represent, respectively, the number of pixels in the longitudinal direction and the number of pixels in the lateral direction of the imaging device 3. In addition, $N_{m0}$ and $N_{n0}$ represent the constants for determining the center coordinates of the BRDF. With respect to B in the expression (1), G(m,n) may become 0, which causes a divergence to occur. In order to prevent such a divergence from occurring, a Wiener filter may be used as in the following expression.

$$B(m, n) = \sum_{n=0}^{N_n-1} \sum_{m=0}^{N_m-1} \frac{I(m, n)}{G(m, n)} \frac{|G(m, n)|^2}{|G(m, n)|^2 + c} \exp\left[\frac{-i2\pi N_{m0}}{N_m} + \frac{-i2\pi N_{n0}}{N_n}\right] \quad (2)$$

Figure 2:
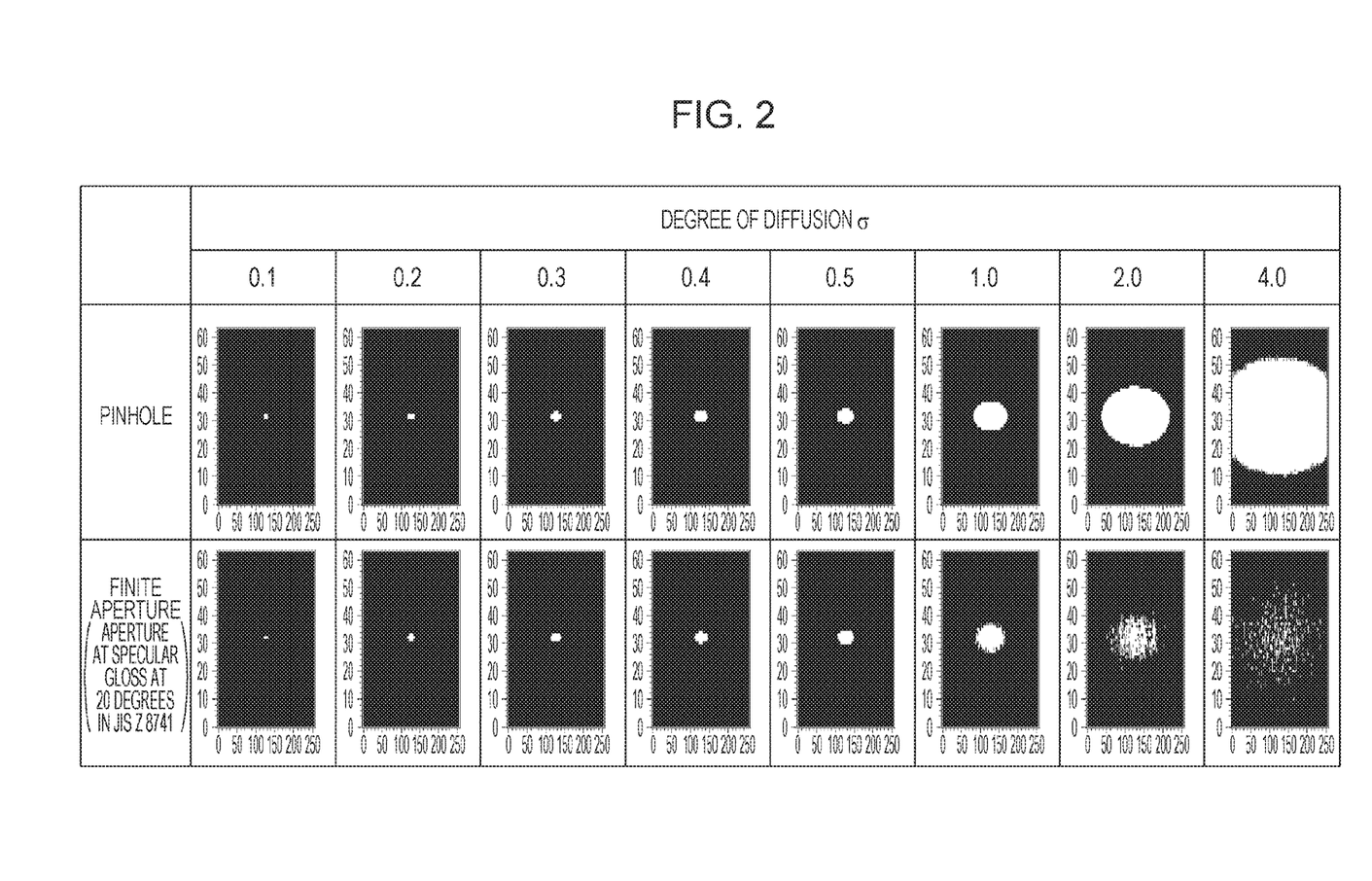
FIG. 2 illustrates a BRDF obtained when a coefficient of a Wiener filter is kept constant regardless of the degree of diffusion.

In the above, the fraction that is not present in the expression (1) corresponds to the Wiener filter, and c represents a Wiener coefficient (also referred to simply as a coefficient). The gain of the filter varies in accordance with the coefficient c. What is important here is that the value of c is determined in accordance with not only G(m,n) that is not dependent on the sample 2 but also I(m,n) that is dependent on the sample 2. Specifically, an ideal value of c varies depending on the degree of diffusion (e.g., the degree of diffusion σ, which will be described later), and c cannot be set to a fixed value. For describing this point, FIG. 2 illustrates a BRDF obtained when the coefficient of the Wiener filter is kept constant regardless of the degree of diffusion. The BRDF obtained when the aperture in the aperture unit 101 is a pinhole (e.g., expressed by a δ function) and the BRDF obtained when the aperture in the aperture unit 101 is an aperture (slit) defined in accordance with the specular gloss at 20 degrees in JIS Z 8741 are illustrated for different degrees of diffusion (Gaussian radius). Here, the focal lengths of the condenser lenses 102 and 103 are both 15.5 mm, the aperture in the aperture unit 101 is an aperture defined in accordance with the specular gloss at 20 degrees in JIS Z 8741 (finite aperture), the (primary) light source is a D65 light source, and the dimensions of each pixel in the imaging device 3 are 7.4 μm by 59.2 μm. The coefficient of the Wiener filter is $10^{-4}$. The BRDFs in FIG. 2 are each binarized with the median value of the BRDF serving as a threshold. The degree of diffusion σ of the sample 2 is given by the following expression.

$$f(\theta) = A \cdot \exp\left[-\frac{(\theta - \theta_0)^2}{\sigma^2}\right] \quad (3)$$

Figure 3:
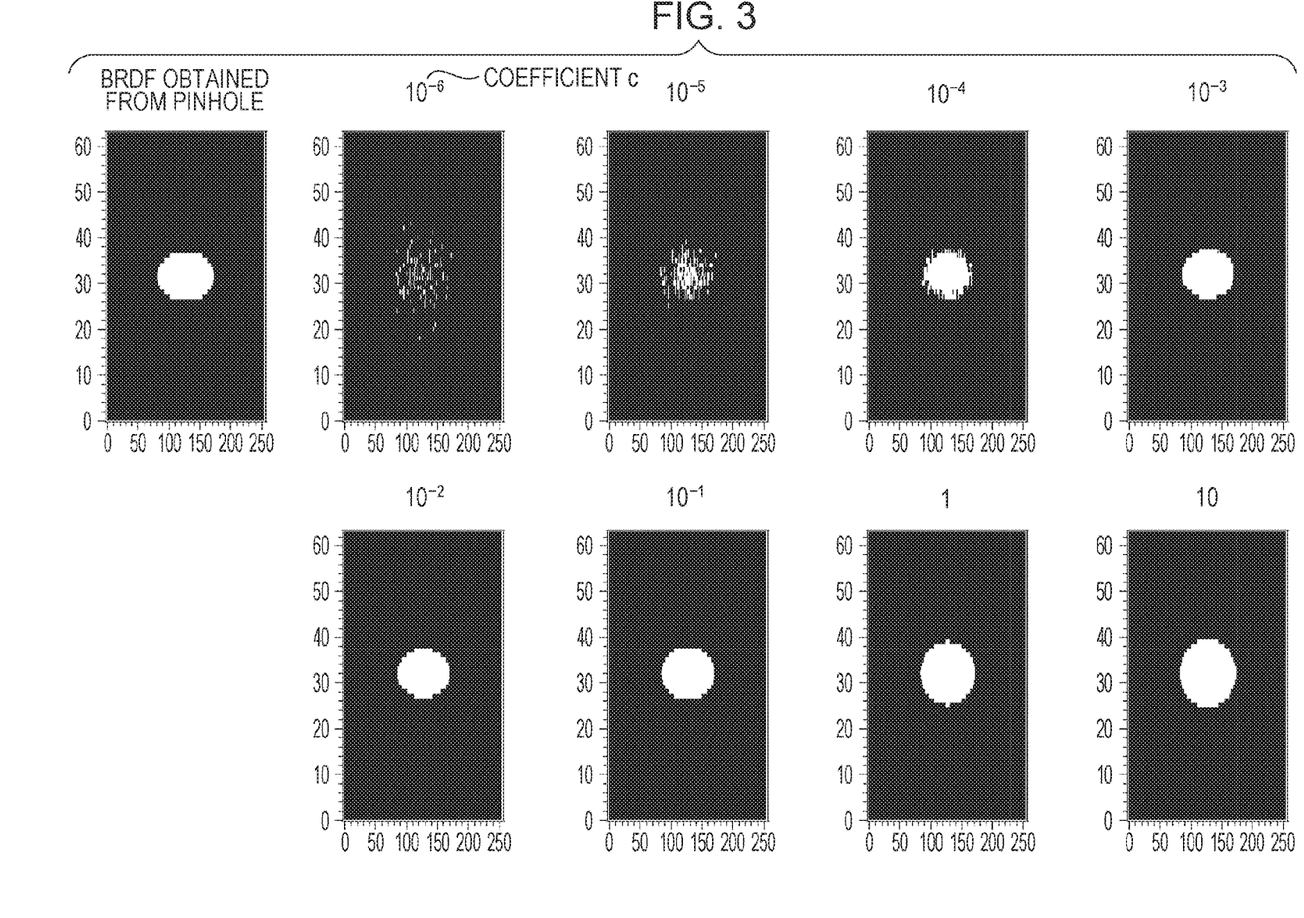
FIG. 3 illustrates a BRDF obtained when a coefficient of a Wiener filter is varied.

In the above, $\theta_0$ represents the specular reflection angle (=20°), and A represents a coefficient for normalizing the reflectance. Referring to FIG. 2, in the case of the finite aperture, the BRDF deviates from the BRDF in the case of the pinhole in accordance with the degree of diffusion σ, and the deviation is greater in particular as the degree of diffusion σ is greater. In this manner, when the coefficient of the Wiener filter is fixed, an appropriate BRDF may not be obtained. With respect to the case of the finite aperture, FIG. 3 illustrates the BRDF obtained when the coefficient of the Wiener filter is varied. In this case, the degree of diffusion σ is set to 1.0, and the coefficient c is varied. FIG. 3 reveals that, when the coefficient c is in a range from around $10^{-3}$ to $10^{-2}$, the obtained BRDF is close to the BRDF obtained in the case of the pinhole and the deviation increases in other ranges. In other words, an appropriate BRDF may be obtained when (the coefficient c of) the Wiener filter is determined in accordance with the degree of diffusion. Referring back to FIG. 1B, processing steps therefor will be described.

In step S3, the degree of diffusion σ is estimated, and the coefficient c of the Wiener filter is determined on the basis of the estimated degree of diffusion σ. In step S4, the Wiener filter is determined on the basis of the coefficient c determined in S3. More specifically, in step S3, a provisional BRDF can be obtained on the basis of a provisional Wiener coefficient c determined in advance, and the degree of diffusion σ can be estimated on the basis of the provisional BRDF. Alternatively, the degree of diffusion σ can be estimated on the basis of a correlation (e.g., a correlation coefficient) between the aperture g and the image i. Specifically, the degree of diffusion of the sample may be estimated on the basis of one of the image and a Fourier transform thereof and one of the (secondary) light source corresponding thereto and a Fourier transform thereof. These methods will be described later in detail with specific examples in a first example and a second example.

Lastly, in step S5, b(θ1,θ2) as the BRDF of the sample 2 is obtained by subjecting B(m,n), which is a Fourier transform of the BRDF, to an inverse Fourier transform, as in the following expression.

$$b(\theta 1, \theta 2) = \text{FFT}^{-1}(B(m,n)) \quad (4)$$

In the above, b(θ1, θ2) as the BRDF of the sample 2 generally takes a nonnegative value, but the BRDF obtained through the expression (4) may take a negative value.

However, the absolute value of such a negative value is small when an appropriate Wiener filter is selected, and thus even when such a negative value is turned into a nonnegative value (i.e., rounding to 0 or turning it into a positive value by taking its absolute value), an influence of such an operation may be negligible. In this manner, an appropriate BRDF can be obtained. Thus, a measuring apparatus that is advantageous in terms of the angular resolution of an obtained optical characteristic can be provided.

Although a case in which the sample reflects light has been illustrated as an example in the foregoing description, the present invention is not limited thereto. For example, the sample may transmit light (the optical characteristic obtained in this case are bidirectional transmittance distribution function (BTDF)). Furthermore, although the reflection characteristic (reflectance) have been described as an example, the present invention is not limited thereto, and the reflection characteristic (reflectance) may be converted to an absorption characteristic (absorptance).

First Example

Figure 4:
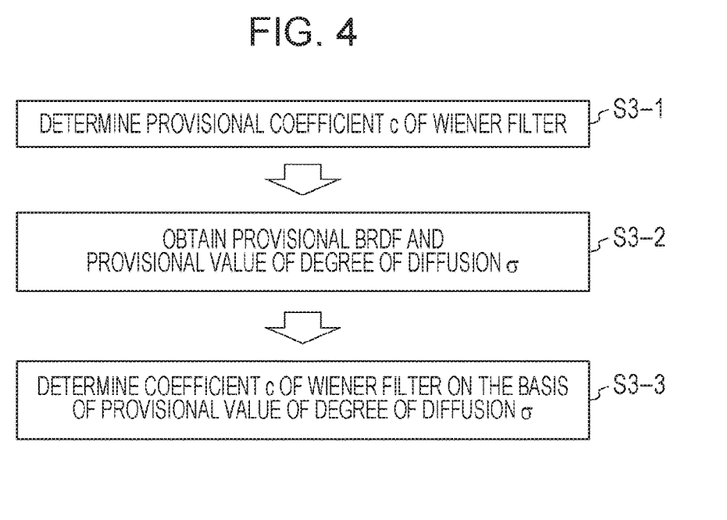
FIG. 4 illustrates an example of a flow of a process of determining a coefficient of a Wiener filter.

FIG. 4 illustrates an example of the flow of the process of determining the coefficient of the Wiener filter. Specifically, FIG. 4 illustrates a specific example of the flow of the process in step S3 of FIG. 1B. In step S3-1, a provisional coefficient c of the Wiener filter is set to a provisional value (predetermined value) determined in advance. Here, the focal lengths of the condenser lenses 102 and 103 are both 15.5 mm, the aperture in the aperture unit 101 is an aperture in accordance with the specular gloss at 20 degrees defined by JIS Z 8741 (finite aperture), the primary light source is a D65 light source, and the dimensions of each pixel in the imaging device 3 are 7.4 μm by 59.2 μm. In this case, the provisional coefficient c of the Wiener filter preferably takes a value within a range from $10^{-3}$ to $10^{-1}$ inclusive. In addition, when the aperture (slit) in the aperture unit 101 is an aperture in accordance with the specular gloss at 60 degrees defined by JIS Z 8741, the provisional coefficient c preferably takes a value within a range from $10^{-2}$ to 1 inclusive.

In step S3-2, a provisional BRDF is obtained on the basis of the provisional filter coefficient c, and a provisional value of the degree of diffusion σ is obtained. When the aperture (slit) in the aperture unit 101 is an aperture in accordance with the specular gloss at 20 degrees, the provisional filter coefficient c is set to $10^{-3}$. With respect to the degree of diffusion σ of the sample, the BRDF is obtained through the expressions (2) and (4) with the use of the provisional filter coefficient c, and the obtained BRDF is fitted through the expression (3). Thus, provisional values of the degree of diffusion σ can be obtained as indicated in Table 1. The aforementioned fitting may be carried out on the degree of diffusion σ with the use of a Gaussian function (the right-hand side of the expression (3)) having the degree of diffusion σ in the form of a Gaussian radius as an unknown.

TABLE 1

| DEGREE OF DIFFUSION σ | PROVISIONAL VALUE OF σ |
|---|---|
| 0.010 | 0.037 |
| 0.020 | 0.045 |
| 0.030 | 0.052 |
| 0.040 | 0.059 |
| 0.050 | 0.067 |
| 0.100 | 0.117 |
| 0.200 | 0.219 |

TABLE 1-continued

| DEGREE OF DIFFUSION σ | PROVISIONAL VALUE OF σ |
|---|---|
| 0.300 | 0.312 |
| 0.400 | 0.415 |
| 0.500 | 0.519 |
| 1.000 | 1.034 |
| 2.000 | 2.032 |
| 4.000 | 4.020 |

In step S3-3, the coefficient c of the Wiener filter is determined on the basis of the provisional value of the degree of diffusion σ obtained in S3-2 with reference to Table 1 and Table 2. Table 2 indicates preferable coefficients (common logarithms) of the Wiener filter obtained in advance with respect to the degree of diffusion σ of the sample 2.

TABLE 2

| DEGREE OF DIFFUSION σ | $\text{Log}_{10}(c)$ |
|---|---|
| 0.01 | −8 |
| 0.02 | −8 |
| 0.03 | −8 |
| 0.04 | −8 |
| 0.05 | −7 |
| 0.1 | −6 |
| 0.2 | −5 |
| 0.3 | −4 |
| 0.4 | −4 |
| 0.5 | −3 |
| 1 | −3 |
| 2 | −3 |
| 4 | −3 |

Figure 5:
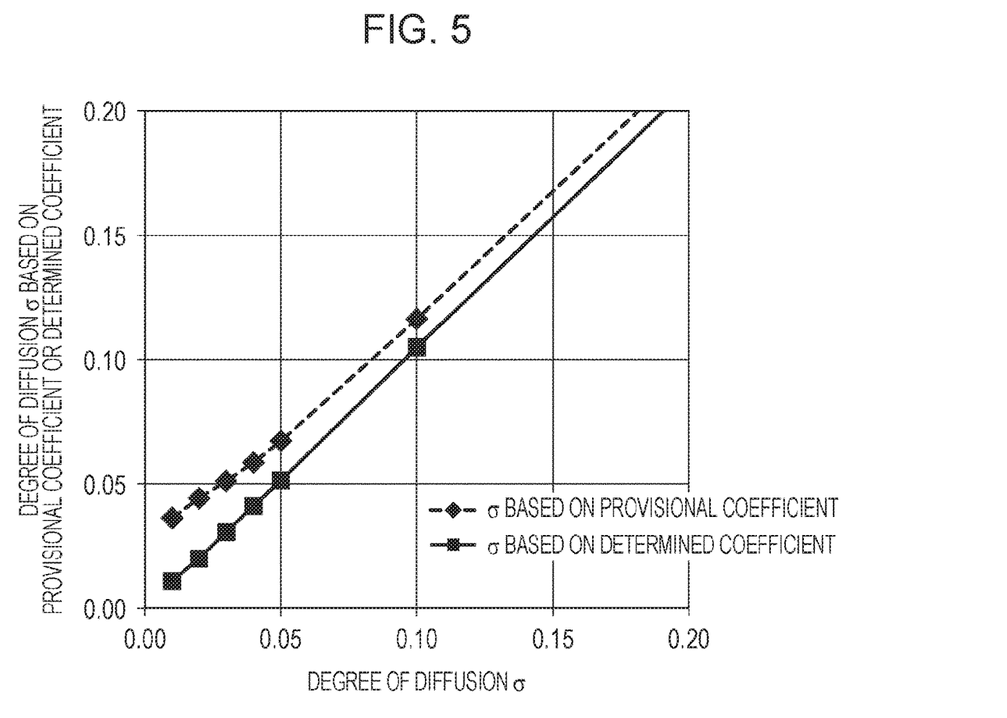
FIG. 5 illustrates the degree of diffusion that is based on a BRDF obtained with the use of a provisional coefficient or a determined coefficient.

FIG. 5 illustrates the degree of diffusion that is based on the BRDF obtained by using the provisional coefficient or the determined coefficient. As compared with (the provisional value of) the degree of diffusion σ obtained from the provisional coefficient, the degree of diffusion σ obtained from the determined coefficient is close to the actual degree of diffusion σ of the sample. This reveals that an effective BRDF can be obtained even when a finite aperture instead of a pinhole is used as the aperture in the aperture unit 101.

Second Example

Figure 6:
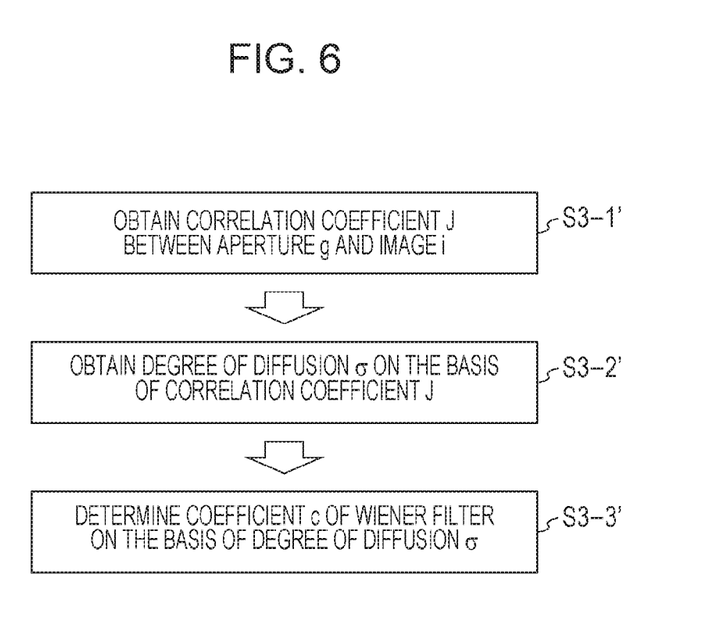
FIG. 6 illustrates another example of a flow of a process of determining a coefficient of a Wiener filter.

FIG. 6 illustrates another example of the flow of the process of determining the coefficient of the Wiener filter. In step S3-1', a correlation (correlation coefficient J in this case) between the aperture g in the aperture unit 101 and the image i is obtained.

$$J = \frac{\sum_{n=0}^{N_n-1} \sum_{m=0}^{N_m-1} \{i(x,y) - i_0\}\{g(x,y) - g_0\}}{\sum_{n=0}^{N_n-1} \sum_{m=0}^{N_m-1} \{i(x,y) - i_0\}^2 \sum_{n=0}^{N_n-1} \sum_{m=0}^{N_m-1} \{g(x,y) - g_0\}^2} \quad (5)$$

In the above, $g_0$ represents a mean value of g(x,y), and $i_0$ represents a mean value of i(x,y).

In step S3-2', the degree of diffusion σ is obtained on the basis of the correlation coefficient J obtained through expression (5) with reference to the relations indicated in Table 3 obtained in advance. The relations indicated in Table 3 are obtained under the same condition as the first example.

TABLE 3

| DEGREE OF DIFFUSION $\sigma$ | CORRELATION COEFFICIENT J |
| --- | --- |
| 0.01 | 1.000 |
| 0.02 | 1.000 |
| 0.03 | 0.999 |
| 0.04 | 0.999 |
| 0.05 | 0.997 |
| 0.1 | 0.989 |
| 0.2 | 0.964 |
| 0.3 | 0.926 |
| 0.4 | 0.876 |
| 0.5 | 0.825 |
| 1 | 0.628 |
| 2 | 0.437 |
| 4 | 0.339 |

In step S3-3', as in the first example, the coefficient c of the Wiener filter is determined on the basis of the degree of diffusion σ obtained in step S3-2' and the relations indicated in Table 2.

The measurement of the specular gloss at 20 degrees has primarily been illustrated as an example in the first exemplary embodiment above, but the present invention is not limited thereto. For example, the aperture (slit) in the aperture unit 101 may be rectangular having different dimensions, may be circular, or may have yet another shape. The angle is not limited to 20 degrees, and various other angles may be employed.

Second Exemplary Embodiment

In the present exemplary embodiment, the angle of aperture 113 on the light-projection side, the angle of aperture 114 on the light-receiving side, the (primary) light source 1, the aperture in the aperture unit 101, and the angle of incidence of light incident on the sample (the angle of reflection of light from the sample) according to the first exemplary embodiment are configured so as to comply with any one of the JIS standards and the ISO standards. Such a configuration makes it possible to output a measurement value in accordance with such standards and to output a general index, such as a BRDF. For example, in order to output a specular gloss as a measurement value, a configuration compliant with JIS Z 8741 may be employed. In addition, in order to output a haze as a measurement, a configuration compliant with ASTM E430 may be employed, or in order to output an image clarity as a measurement value, a configuration compliant with JIS K 7374 may be employed. In order to output a general index, such as a BRDF, in the aforementioned configuration, processing that follows the flow of the process described with reference to FIG. 1B, FIG. 4, or FIG. 6 in the first exemplary embodiment may be carried out.

Thus far, exemplary embodiments of the present invention have been described, but it is needless to say that the present invention is not limited to these exemplary embodiments, and various modifications and changes can be made within the scope of spirit of the present invention. For example, the processor 4 may obtain a BRDF as the optical characteristic and may obtain at least one of the gloss, the haze, the DOI, and the image clarity as the optical characteristic on the basis of the obtained BRDF. In this case, an image of the aperture may be taken (computed) from the aperture (e.g., g(x,y) described above) in the aperture unit 101 that is compliant with the standards and the BRDF (e.g., b(θ1, θ2) described above), and the optical characteristic compliant with the standards may be obtained on the basis of the stated image.

In addition, when an influence of aberration of the optical system in the measuring apparatus is not negligible, the optical characteristic may be obtained through the expression (2) after (the influence of) the aberration on the image (e.g., i(x,y) or I(m,n) described above) obtained through the optical system has been compensated for. In this case, with the use of a Wiener filter that is based on the characteristic of the stated aberration (transfer function), a restored (recovered) image I'(m,n) of which aberration has been compensated for may be used in place of I(m,n).

In addition, in the examples described above, the degree of diffusion of the sample is estimated on the basis of one of the image and the Fourier transform thereof and one of the light source corresponding thereto and the Fourier transform thereof, and the coefficient of the Wiener filter is determined on the basis of the degree of diffusion obtained from the estimation. However, the present invention is not limited thereto. For example, the coefficient may be determined not on the basis of (the estimated value) of the degree of diffusion of the sample but on the basis of other information (data), such as information correlated to (the estimated value) of the degree of diffusion. For example, the coefficient may be determined on the basis of at least one of the provisional BRDF described above and the correlation coefficient. Furthermore, the coefficient may be determined on the basis of one of the image used to obtain the provisional BRDF and the correlation coefficient and the Fourier transform thereof or a feature amount thereof and one of the light source corresponding thereto and the Fourier transform thereof or a feature amount thereof. In addition, the information in Table 2 that indicates coefficients (their common logarithms) suitable for the degree of diffusion of the sample is obtained in advance, but the present invention is not limited thereto and does not exclude a mode in which such information is obtained for each instance. This also applies in a case in which other information different from (the estimated value) of the degree of diffusion of the sample as described above is used.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-096830 filed May 11, 2015, which is hereby incorporated by reference herein in its entirety.

What is claimed is:

1. A measuring apparatus comprising:
   an imaging device including plural pixels arranged in a matrix form and configured to take an image of a light source by the plural pixels;
   an optical system configured to project light from the light source onto a sample and to guide light regularly reflected on the sample to the imaging device; and
   a processor configured to obtain an optical characteristic of the sample based on an output of the imaging device, wherein the processor is configured to
      estimate a degree of diffusion for the projected light of the sample based on one of the image and the Fourier transform thereof and one of the light source and the Fourier transform thereof,
      determine a coefficient of a Wiener filter based on the estimated degree of diffusion, and
      obtain the optical characteristic based on the Wiener filter of which the coefficient has been determined, the Fourier transform of the image, and the Fourier transform of the light source.

2. The measuring apparatus according to claim 1, wherein the processor is configured to
   obtain a provisional optical characteristic based on a provisional Wiener filter of which the coefficient is a predetermined value, the Fourier transform of the image, and the Fourier transform of the light source, and
   estimate the degree of diffusion based on the obtained provisional optical characteristic.

3. The measuring apparatus according to claim 2, wherein the processor is configured to obtain a bidirectional reflectance distribution function as the provisional optical characteristic.

4. The measuring apparatus according to claim 3, wherein the processor is configured to estimate the degree of diffusion based on a Gaussian function having the degree of diffusion as an unknown Gaussian radius and the bidirectional reflectance distribution function.

5. The measuring apparatus according to claim 1, wherein the processor is configured to estimate the degree of diffusion based on a correlation between the image and the light source.

6. The measuring apparatus according to claim 5, wherein the processor is configured to obtain, as the correlation, a correlation coefficient between the image and the light source.

7. The measuring apparatus according to claim 1, wherein coefficients of Wiener filters used for the plural pixels forming the image all have a same value.

8. The measuring apparatus according to claim 1, wherein the processor is configured to obtain, as the optical characteristic, at least one of a bidirectional reflectance distribution function, a gloss, a haze, a distinctness of image, and an image clarity.

9. The measuring apparatus according to claim 1,
   wherein the processor is configured to
      obtain a bidirectional reflectance distribution function as the optical characteristic, and
      obtain, as the optical characteristic, at least one of a gloss, a haze, a distinctness of image, and an image clarity based on the obtained bidirectional reflectance distribution function.

10. A measuring method for obtaining an optical characteristic of a sample, the method comprising steps of:
    projecting light from a light source onto the sample and guiding light regularly reflected on the sample to an imaging device;
    taking an image of the light source via the sample using the imaging device;
    estimating a degree of diffusion for the projected light of the sample based on one of the image and the Fourier transform thereof and one of the light source and the Fourier transform thereof; and
    determining a coefficient of a Wiener filter based on the estimated degree of diffusion; and
    obtaining the optical characteristic based on the Wiener filter of which the coefficient has been determined, the Fourier transform of the image, and the Fourier transform of the light source.

11. A computer-readable non-transitory storage medium that stores a program for causing a computer to execute steps of a measuring method for obtaining an optical characteristic of a sample, the method including steps of:
    projecting light from a light source onto the sample and guiding light regularly reflected on the sample to an imaging device;
    taking an image of the light source via the sample using the imaging device;
    estimating a degree of diffusion for the projected light of the sample based on one of the image and the Fourier transform thereof and one of the light source and the Fourier transform thereof;
    determining a coefficient of a Wiener filter based on the estimated degree of diffusion; and
    obtaining the optical characteristic based on the Wiener filter of which the coefficient has been determined, the Fourier transform of the image, and the Fourier transform of the light source.

* * * * *